United States Patent

Mehrhof et al.

[11] 3,985,881
[45] Oct. 12, 1976

[54] 1(3,4,5-TRIMETHOXYBENZAMIDO METHYL) TETRAHYDRO ISOQUINOLINE DERIVATIVES AND A PROCESS FOR THEIR PRODUCTION

[75] Inventors: Werner Mehrhof; Rolf Pohlke; Karl Heinz Becker; Hans-Jochen Schliep, all of Darmstadt, Germany

[73] Assignee: Merck Patent Gesellschaft mit beschrankter Haftung, Darmstadt, Germany

[22] Filed: Dec. 9, 1974

[21] Appl. No.: 530,551

[30] Foreign Application Priority Data
Dec. 10, 1973 Germany............................ 2361390

[52] U.S. Cl................... 424/258; 260/247.2 A; 260/247.5 R; 260/286 R; 260/286 Q; 260/287 D; 260/293.87; 260/471 A; 260/471 C; 260/476 R; 260/551 R; 260/569; 260/571
[51] Int. Cl.²...................................... C07D 217/12
[58] Field of Search ........ 260/287 D, 287 F, 287 R; 424/258

[56] References Cited
UNITED STATES PATENTS

| | | | |
|---|---|---|---|
| 2,612,503 | 9/1952 | Ullyot............................ | 260/287 D |
| 2,640,829 | 6/1953 | Wilson et al..................... | 260/287 D |
| 3,021,331 | 2/1962 | Lombardino et al. .......... | 260/287 D |
| 3,483,206 | 12/1969 | Werner.......................... | 260/287 D |
| 3,600,394 | 8/1971 | Coyne et al.................... | 260/287 D |

OTHER PUBLICATIONS
Leonard et al., "JACS," 1949, pp. 3405–3408, from CA. 45:167d.
Burger, "Medicinal Chemistry," pp. 42–497, 1966.

*Primary Examiner*—Nicholas S. Rizzo
*Assistant Examiner*—David E. Wheeler
*Attorney, Agent, or Firm*—Millen, Raptes & White

[57] ABSTRACT

Novel isoquinoline derivatives of the formula

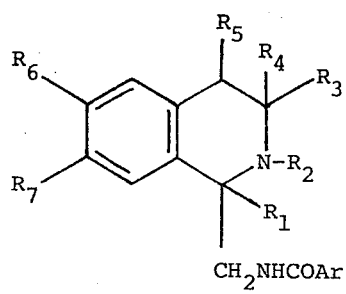

wherein $R_1$ is H or, together with $R_2$, a C—N bond; $R_2$ is H, $R_8$ or, together with $R_1$, a C—N bond; $R_3$ is H, methyl or ethyl; $R_4$ and $R_5$ each are H or collectively a C—C bond; and $R_6$ and $R_7$ each are H or methoxy; $R_8$ being acyl of 1–10 carbon atoms or alkyl of 1–17 carbon atoms optionally mono- or polysubstituted by phenyl, OH, ArCOO—, ArCONH—, piperidino, 3,4-dehydropiperidino, morpholino, carboxy, carbomethoxy and/or carbethoxy, Ar being 3,4,5-trimethoxyphenyl; and the physiologically acceptable acid addition salts and quaternary ammonium salts thereof, have cardiovascular activity and can be prepared by acylating a corresponding primary amine lacking the COAr group with 3,4,5-trimethoxybenzoic acid or a functional derivative thereof.

27 Claims, No Drawings

1(3,4,5-TRIMETHOXYBENZAMIDO METHYL) TETRAHYDRO ISOQUINOLINE DERIVATIVES AND A PROCESS FOR THEIR PRODUCTION

BACKGROUND OF THE INVENTION

This invention relates to novel isoquinoline derivatives.

SUMMARY OF THE INVENTION

In a composition aspect, this invention relates to novel isoquinoline derivatives of the general Formula I

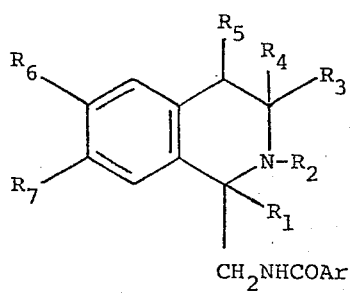

wherein $R_1$ is H or, together with $R_2$, a C—N bond; $R_2$ is H, $R_8$ or, together with $R_1$, a C—N bond; $R_3$ is H, methyl or ethyl; $R_4$ and $R_5$ each are H or collectively a C—C bond; and $R_6$ and $R_7$ each are H or methoxy; $R_8$ being acyl of 1–10 carbon atoms or alkyl of 1—17 carbon atoms optionally mono- or polysubstituted by one, two or more of phenyl, OH, ArCOO—, ArCONH—, piperidino, 3,4-dehydropiperidino, morpholino, carboxy, carbomethoxy and/or carbethoxy, Ar being 3,4,5-trimethoxyphenyl, and the physiologically acceptable acid addition salts and quaternary ammonium salts thereof.

In another composition aspect, this invention relates to pharmaceutical compositions one or more compounds of this invention.

In process aspects, this invention relates to processes for the production of compounds of this invention and their use to achieve cardiovascular effects.

DETAILED DISCUSSION

In Formula I, $R_1$, $R_2$, $R_4$, $R_5$, $R_6$ and $R_7$ preferably are H, and $R_3$ is preferably H or methyl.

$R_8$ preferably is alkanoyl of 1–10, preferably 2–7, carbon atoms, benzoyl, substituted benzoyl, e.g., benzoyl substituted by one or more, preferably 1–3 alkoxy groups, such as o-, m- or p-methoxybenzoyl or 3,4,5-trimethoxybenzoyl, alkyl of preferably 1–4 carbon atoms, alkyl substituted by phenyl, e.g., benzyl or 2-phenylethyl, alkyl substituted by a hydroxy group, preferably in the β- or γ-position, e.g., 2-hydroxyethyl or 3-hydroxypropyl, ArCOO-alkyl, e.g., 2-(3,4,5-trimethoxybenzoyloxy)-ethyl or 3-(3,4,5-trimethoxybenzoyloxy)-propyl, ArCONH-alkyl, e.g., 2-(3,4,5-trimethoxy-benzamido)-ethyl or 3-(3,4,5-trimethoxybenzamido)-propyl, piperidinoalkyl, e.g., 2-piperidinoethyl, 2- or 3-piperidino-propyl, 3,4-dehydropiperidinoalkyl, e.g., 2-(3,4-dehydropiperidino)-ethyl, 2- or 3-(3,4-dehydropiperidino)-propyl, morpholinoalkyl, e.g., 2-morpholinoethyl, 2- or 3-morpholinopropyl, carboxyalkyl, e.g., 2-carboxyethyl, 2- or 3-carboxypropyl, carbomethoxyalkyl, or carbethoxyalkyl, wherein the alkyl group of the above-named substituted alkyl groups contains 1–4, preferably 2 or 3, carbon atoms, and alkyl groups bearing two different substituents, e.g., 2-(3,4,5-trimethoxybenzoyloxy)-3-morpholinopropyl.

Examples of alkanoyl are formyl, acetyl, propionyl, butyryl, isobutyryl, valeryl, hexanoyl, heptanoyl, octanoyl, nonanoyl or decanoyl, Alkyl preferably is methyl, ethyl, n-propyl, or n-butyl, but can also be isopropyl, isobutyl, sec.-butyl and tert-butyl, etc.

The compounds of Formula I are preferably tetrahydro-isoquinolines, but can also be isoquinolines, 1,2-dihydroiso-quinolines and 3,4-dihydroisoquinolines.

Among the compounds of Formula I, preferred are those wherein at least one of the $R_1$ through $R_5$ groups has one of the preferred values given above. An especially preferred class of compounds are 1-(3,4,5-trimethoxybenzamidomethyl)-3-methyl-1,2,3,4-tetrahydroisoquinoline and the physiologically acceptable acid addition salts thereof.

In a process aspect, this invention relates to a process for the production of the compounds of Formula I, as well as the physiologically acceptable acid addition salts and quaternary ammonium salts thereof, by a. reacting a compound of general Formula II

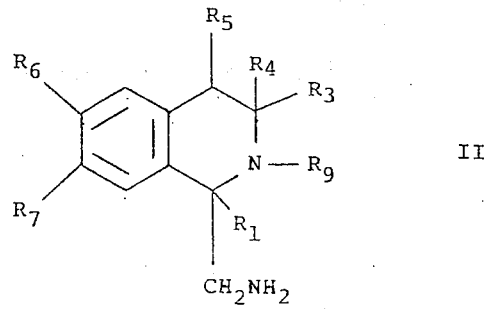

wherein $R_9$ is $R_2$ or alkyl of 1-4 carbon atoms substituted by $NH_2$, with 3,4,5-trimethoxybenzoic acid or a functionally reactive derivative thereof; or b. treating a compound of general Formula III

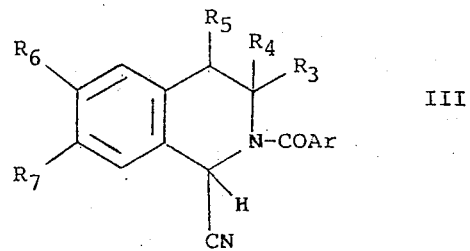

with a reducing agent; or c. reacting a compound of general Formula IV

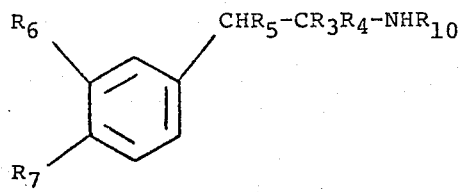

IV wherein $R_{10}$ is H, alkyl of up to 1–17 carbon atoms or a corresponding alkyl mono- or polysubstituted by phenyl, OH, ArCOO—, ArCONH—, piperidino, 3,4-dehydropiperidino, morpholino, carboxy, carbomethoxy and carbethoxy with 3,4,5-trimethoxy-benzamidoacetaldehyde or a functional derivative thereof; or d. treating a compound of general Formula V

  V wherein $R_{11}$ is

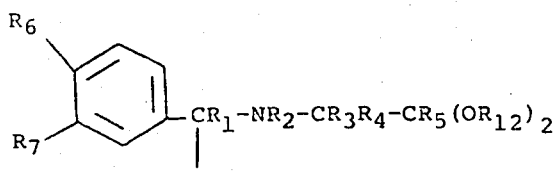

or

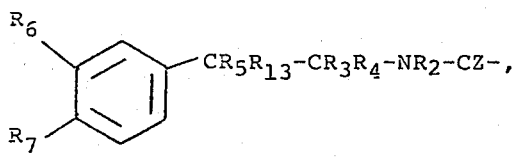

$R_{12}$ is alkyl of 1–4 carbon atoms, $R_{13}$ is H, OH or $OCH_3$ and Z is O or S, with a cyclizing agent; or e. reacting a compound of Formula VI

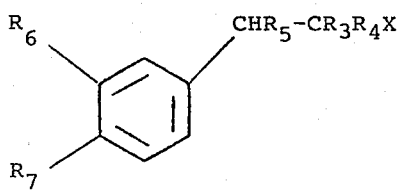

VI wherein X is a halogen atom or a reactively esterified OH-group, with 3,4,5-trimethoxybenzamidoacetonitrile in the presence of a catalyst.

Optionally thereafter, the $R_8$ group of thus-obtained product is removed by treatment with solvolyzing or hydrogenolyzing agents and/or a hydrogen atom present in the 2-position of the isoquinoline ring is replaced by an $R_8$ group by treatment with a compound of the formula $R_8$—OH or a functional derivative thereof, and/or any double bonds present in the 1(2)-position and/or 3(4)-position are hydrogenated by treatment with a reducing agent, and/or one or two double bonds are introduced into the 1(2)- and/or 3(4)-position by treatment with dehydrogenating agents, and/or that a base of Formula I is converted into a physiologically acceptable acid addition salt thereof by treatment with an acid or into a physiologically acceptable quaternary ammonium salts thereof by treatment with a quaternizing agent, and/or that a thus-obtained quaternary isoquinolinium salt is converted into the corresponding 1,2,3,4-tetrahydroisoquinoline derivative by treatment with a reducing agent.

In Formulae II through VI, $R_1$–$R_8$ and Ar have the values given for Formula I.

$R_9$ preferably is H or one of the preferred groups given above for $R_8$. When $R_9$ is an alkyl group substituted by $NH_2$, the group preferably is 2-aminoethyl or 3-aminopropyl.

$R_{10}$ preferably is H, alkyl of 1–4 carbon atoms or a substituted alkyl given above for $R_5$. $R_{12}$ is preferably methyl or ethyl and $R_{13}$ is preferably H or OH. Z is preferably O. X is preferably Cl or Br, but can also be, for example, I, alkylsulfonyloxy, preferably of 1–6 carbon atoms, or arylsulfonyloxy, preferably of 6–10 carbon atoms.

The above reactions are all conducted according to methods known per se and described in detail in the literature.

The compounds of Formula I are preferably produced by the acylation of the primary amines II with 3,4,5-trimethoxy-benzoic acid (Ar—COOH) or a functional derivative thereof. Suitable functional derivatives are the chloride (ArCOCl), which is preferred, the bromide, the anhydride and the azide. The reaction is carried out in the absence or, more suitably, in the presence of an additional solvent, e.g., a hydrocarbon, such as benzene or toluene; an ether, such as diisopropyl ether, tetrahydrofuran (THF), or dioxane; or a halogenated hydrocarbon, such as dichloromethane, chloroform, carbon tetrachloride or chlorobenzene. It is also suitable to add an inorganic base during the acylation, e.g., an alkali metal or alkaline earth metal hydroxide or carbonate, such as NaOH, KOH, Ca(OH)$_2$ or Na$_2$CO$_3$, a heterocyclic base, such as pyridine or an alkyl pyridine, a trialkylamine, such as triethylamine or triisopropylamine. An excess of this base can also serve as the solvent. The reaction is conducted at about 0° to about 200°, suitably between about 0° and the boiling point of the solvent employed, preferably about 20° to 30°. The reaction times range from about 30 minutes to 7 days. When using the acid itself (Ar—COOH), the reaction can also be accomplished in the presence of an agent which splits off water, such as a carbodiimide, e.g., dicyclohexyl-carbodiimide.

An especially preferred mode of operation resides in reacting the amine II with the chloride (ArCOCl) in pyridine at room temperature.

With this mode of operation, it is also possible to produce the acid halogenide, especially the chloride, in situ from the acid ArCOOH and halogenating reagents, for example, with $SiCl_4$, $PCl_3$, $PBr_3$, $POCl_3$, $SOCl_2$ or $PCl_5$, advantageously in an inert solvent, such as methylene chloride, or an organic base, such as pyridine, at temperatures of about 20° to 200°, preferably about 70° to 140°. The acylation can be conducted with racemic as well as optically active amines II.

When $R_9$ in the starting compound II is hydrogen, the reaction can also lead to diacylated products of Formula I ($R_2$ = ArCO). These compounds are formed as by-products when using an excess of II. In contrast thereto, they are obtained as the primary product if an excess of the acylating agent is utilized.

If amines of Formula II are employed wherein $R_9$ is an alkyl substituted by $NH_2$, the acylation yields final products of Formula I wherein $R_2$ = alkyl substituted by ArCONH. In this case, the acylating agent is suitably employed in a molar ratio of 2:1 (based on II) or in an excess. Similar considerations apply for the starting compounds II wherein $R_9$ is a hydroxyalkyl group. The latter can likewise be acylated, if desired, for example by the use of an excess of the acylating agent, thus obtaining products of Formula I wherein $R_2$ = ArCOO-alkyl.

The isoquinoline derivatives of Formula I are also obtainable by reduction of the Reissert compounds of Formula III which, in turn, are obtained by successive reaction of corresponding isoquinolines and/or 3,4-dihydroisoquinolines with alkalii metal cyanides and ArCOCl.

The reduction is suitably accomplished with catalytically activated hydrogen, the ArCO-group migrating from the ring N-atom to the intermediarily produced amino group in the side chain. For the hydrogenation, one of the customary noble metal, nickel or cobalt catalysts is advantageously employed. The noble metal catalysts can be present on supports (e.g.,platinum or palladium on charcoal [carbon], palladium on calcium carbonate or strontium carbonate), in the form of oxide catalysts (e.g., platinum oxide), or as finely divided metallic catalysts. Nickel and cobalt are suitably used as Raney metals or on kieselguhr or pumice as the support. The hydrogenation can be conducted at pressures of between about 1 and 200 atmospheres and at temperatures of between about −80° and +150°. Suitable solvents include an alcohol, such as methanol, ethanol, isopropanol, n-butanol; an ester, such as ethyl acetate; an ether, such as THF or dioxane; a carboxylic acid, such as acetic acid; or a solvent mixture, e.g., a mixture of water and one of the aforementioned organic solvents. Especially preferred for the reduction of the Reissert compound (III) is Raney nickel under an elevated pressure (about 60–120 atmospheres) and an elevated temperature (about 60°-100°).

The isoquinoline derivatives of Formula I are also obtainable according to the methods customary for isoquinoline syntheses. For example, an amine of Formula IV can be reacted with 3,4,5 -trimethoxybenzamidoacetaldehyde under the conditions of the Pictet-Spengler reaction, thus producing tetrahydroisoquinolines of Formula ($R_1$ = $R_4$ = $R_5$ = H). The phenylethylamines IV are in part known and are obtainable according to conventional methods, for example by the condensation of the corresponding benzaldehyde with a nitroalkane, such as nitromethane, subsequent reduction, and optionally subsequent substitution reactions on the amino group. In place of the aldehyde, it is possible to use one of the functional derivatives thereof, e.g., an acetal, such as the dimethylacetal or diiethylacetal (obtainable, for example, by reacting the corresponding aminoacetaldehyde acetal with ArCOCl). The reaction is accomplished preferably at ph values of below 7, suitably in the presence of an acid, such as hydrochloric acid, sulfuric acid, formic acid, or also in a weakly acidic buffer mixture at temperatures of about 0° to 150°, preferably 20°-100°.

Furthermore, the isoquinoline derivatives I can be produced by the cyclization of the amines V according to the methods of the Pomeranz-Fritsch reaction and-/or the Bischler-Napieralski reaction.

The starting compounds V are obtainable according to various methods known per se. For example, the oxime of an $\alpha$-ArCONH-3-$R_7$-4-$R_6$-acetophenone can be reduced and the thus-obtained primary amine can then be reacted with a chloroacetaldehyde-dialkylacetal. On the other hand, it is possible to react a corresponding phenylethylamine with 3,4,5-trimethoxybenzamidoacetyl chloride to an intermediate product of the formula 3-$R_6$-4-$R_7$-phenyl—$CR_5R_{13}$—$CR_3R_4$N-H—CO—$CH_2$NHCOAr.

The cyclization of V is suitably accomplished with the aid of an acidic cyclization agent. Examples for such agents are acids, including mineral acids, e.g., sulfuric acid, hydrochloric acid and phosphoric acid, Lewis acids, such as $AlCl_3$, $BF_3$ and the derivatives thereof, e.g., $BF_3$-etherate, $SnCl_4$ and acid chlorides, such as $PCl_5$. The cyclization can be effected in the presence or absence of additional inert solvents (e.g., chloroform) at temperatures of about 0° to about 150°, preferably about 20° to 100°. Reaction times of about 1 hour to about 3 days are usually required.

The isoquinoline derivatives I are also obtainable by reacting the halogen compounds (and/or active esters) VI with 3,4,5-trimethoxybenzamidoacetonitrile. The starting compounds VI are generally known and can be prepared according to methods disclosed in the literature, for example from the corresponding phenylethanols by reaction with a halogenating agent or sulfonic acid chloride. The reaction of VI with the aforementioned nitrile is accomplished, for example, in the presence of a cyclization agent, e.g., a Lewis acid, such as $SnCl_4$ or one of the other above-mentioned compounds. An inert solvent, such as chloroform, ethylene chloride, or o-dichlorobenzene can be present. The reaction temperatures range suitably from 0° to 150°, preferably 20° to 110°. Reaction times of about 1 hour to about 48 hours are usually necessary.

A thus-obtained product of Formula I can be converted into another product of Formula I, if desired. Thus, it is possible to remove an $R_8$ group by solvolysis or preferably by hydrogenolysis. For example, an N-benzyl group can be removed by hydrogenolysis under the hydrogenation conditions indicated above. The hydrogenolysis preferably is conducted employing a noble metal catalyst, such as palladium charcoal, at room temperature and under normal or slightly elevated pressure, e.g., up to about 10 atmospheres.

A compound of Formula I ($R_2$ = H) can also be converted according to conventional N-acylation or N- alkylation methods by treatment with a compound of the formula $R_8$—OH or with a functional derivative thereof, thus obtaining a compound of Formula I wherein $R_2 = R_8$.

Suitable acylating agents include not only the free acids of the formula $R_8$—OH ($R_8$ = acyl of 1–10 carbon atoms) but also the functional derivatives thereof, e.g., the corresponding acid chlorides and acid anhydrides. Alkylation can be effected both with alcohols of the formula $R_8$—OH wherein $R_8$ = alkyl of up to 1–17 carbon atoms, optionally substituted as indicated, but also with the corresponding halogenides (chlorides, bromides, iodides).

During the acylation or alkylation, the process is suitably carried out in the presence of a basic catalyst, such as pyridine or triethylamine and/or in the presence of an inert solvent. More specifically, the catalysts and solvents described hereinabove for the acylation of compounds II can be employed, using the other conditions described for use therewith.

A thus-obtained isoquinoline or dihydroisoquinoline derivative of Formula I ($R_1$ and $R_2$ together form a C—N bond and/or $R_4$ and $R_5$ together form a C—C bond) can be converted into the corresponding tetrahydroisoquinoline derivative I ($R_1 = R_2 = R_4 = R_5 =$ H) by treatment with a reducing agent. Suitably, the method of catalytic hydrogenation described above is utilized in this procedure. Preferably, a noble metal catalyst, such as platinum or platinum oxide is employed, and normal pressure and temperatures of about 20° to about 100° are employed.

A thus-obtained dihydro- or tetrahydroisoquinoline derivative can optionally be converted into the corresponding isoquinoline derivative by treatment with a dehydrogenating agent, such as sulfur, selenium or platinum, palladium, nickel or cobalt catalyst, selenium dioxide, dialkyl disulfide, chloranil, or other gently effective oxidizing agent. The dehydrogenation reactions take place suitably in the presence or absence of an inert solvent, such as benzene, toluene or p-cymene at temperatures of about 70° to about 300°.

A base of Formula I can be converted into an acid addition salt thereof with an acid in the usual manner. Suitable for this reaction are those acids yielding physiologically acceptable salts. Thus, inorganic or organic acids can be used, e.g., sulfuric acid, nitric acid, hydrohalic acids, such as hydrochloric or hydrobromic acid, phosphoric acids, such as orthophosphoric acid, also aliphatic, alicyclic, araliphatic, aromatic or heterocyclic mono- or polybasic carboxylic or sulfonic acids, such as formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicylic acid, phenylpropionic acid, citric acid, gluconic acid, ascorbic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and - disulfonic acids. The free bases of Formula I can be liberated from their acid addition salts by treatment with a strong base, such as sodium or potassium hydroxide, sodium or potassium carbonate.

Bases of Formula I can be converted into the corresponding quaternary salts by treatment with a quaternizing agent in accordance with methods known from the literature. Suitable as quaternizing agents are, for example, alkyl halogenides, such as methyl iodide, and dialkyl sulfates, such as dimethyl sulfate.

Quaternary salts thus obtained can be reduced to the corresponding 1,2,3,4-tetrahydroisoquinoline derivatives in accordance with methods disclosed in the literature, for example by catalytic hydrogenation under the aforementioned conditions, preferably on a noble metal catalyst, such as Pd at about 20°–60° and 1–5 atmospheres, or by reaction with sodium borohydride, e.g., in methanol at room temperature.

If the compounds of Formula I contain a center of asymmetry, they are ordinarily obtained in their racemic form. If the compounds have two or more centers of asymmetry, they are obtained during the synthesis generally as mixtures of racemates, from which the individual racemates can be isolated, for example, by repeated recrystallization from suitable solvents and can thus be obtained in the pure form.

The thus-produced racemates can be separated into their optical antipodes by conventional mechanical or chemical methods. Preferably, diastereomers are formed from the racemic mixture by reaction with an optically active resolving agent. Suitable resolving agents are, for example, optically active acids, such as D- and L-tartaric acid, dibenzoly-D- and -L-tartaric acid, diacetyl-D- and -L-tartaric acid, β-camphorsulfonic acid, D- and L-mandelic acid, D- and L-malic acid, or D- and L-lactic acid.

It is, of course, possible to obtain optically active compounds according to the above-described methods by using starting compounds which are optically active.

The compounds of this invention possess valuable pharmacological properties. In particular, they produce beneficial effects on the heart and the circulation. Their anti-arrhythmic activity is particularly significant. Arrhythmia induced in rats by potassium can be overcome by oral administration of a compound of Formula I or a salt thereof. The compounds of this invention also have analgesic activity, as evidenced in an intravasal pain model on dogs. This component of activity is of significance in pain conditions occurring in cases of angina pectoris. Furthermore, high activities were observed in several infarction models, for example in the suppression of the ramus descendens paraconalis of the arteria coronaria sinistra in dogs.

The compounds of this invention thus are useful as medicinal agents. They can also be used as intermediates for the manufacture of other medicines.

The novel compounds of Formula I and/or optionally the physiologically acceptable acid addition salts thereof can be used as medicinal agents in a mixture with solid, liquid and/or semi-liquid excipients in the human or veterinary medicine. Suitable vehicles are those organic or inorganic materials amenable to parenteral, enteral or topical application and which do not react with the novel compounds, such as, for example, water, vegetable oils, polyethylene glycols, gelatin, lactose, amylose, magnesium stearate, talc, vaseline, cholesterol. Suitable for parenteral application are, in particular, solutions, preferably oily or aqueous solutions, as well as suspensions, emulsions, or implants. Suitable for enteral application are tablets, dragees, capsules, syrups, elixirs, or suppositories, and for topical application ointments, creams or powders. The above-indicated preparations can optionally be sterilized or mixed with auxiliary agents, such as preservatives, stabilizers or wetting agents, salts for influencing the osmotic pressure, buffer substances, coloring agents, flavoring agents and/or aromatic substances.

The compounds of this invention are administered to lower animals orally preferably in doses of about 1 to 500, preferably 2 to 100 mg., per kg. of body weight. In human patients, the oral doses are normally somewhat lower, viz., preferably 20 to 500 mg. per dosage unit is administered.

The temperatures herein are indicated in degrees Celsius.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. A solution of 17.6 g. of 1-aminomethyl-3-methyl-1,2,3,4-tetrahydroisoquinoline and 26.8 g. of 3,4,5-trimethoxybenzoyl chloride in 120 ml. of pyridine is allowed to stand for 2 days at 20°. The mixture is then evaporated, the residue taken up in chloroform, and repeatedly washed with 5% potassium bicarbonate solution. After drying, evaporation, and recrystallization of the residue from ether, 1-(3,4,5-trimethoxybenzamidomethyl)-3-methyl-1,2,3,4-tetrahydroisoquinoline is obtained, m.p. 162°–164°. From the ether filtrate, a small amount of oily 1-(3,4,5-trimethoxybenzamidomethyl)-2-(3,4,5-trimethoxybenzoyl)-3-methyl-1,2,3,4-tetrahydroisoquinoline can be isolated.

Analogously, using the following starting compounds:

1-aminomethyl-isoquinoline
1-aminomethyl-3-methyl-isoquinoline
1-aminomethyl-3-ethyl-isoquinoline
1-aminomethyl-3-ethyl-1,2,3,4-tetrahydroisoquinoline
1-aminomethyl-2-benzyl-1,2,3,4-tetrahydroisoquinoline
1-aminomethyl-2-(2-piperidinoethyl)-1,2,3,4-tetrahydroisoquinoline [obtainable by reacting 1-benzamidomethyl-2-(2-chloroethyl)-1,2,3,4-tetrahydroisoquinoline with pyridine to the quaternary salt, hyrogenation of the pyridine ring, and splitting off the benzoyl group with hydrochloric acid]
1-aminomethyl-2-[2-(3,4-dehydropiperidino)-ethyl]-1,2,3,4-tetrahydroisoquinoline (obtainable by reduction of the above quaternary salt with NaBH₄ and subsequent splitting by hydrolysis)
1-aminomethyl-2-(3-carbethoxypropyl)-1,2,3,4-tetrahydroisoquinoline [obtainable by reacting 1-benzamidomethyl-2-(2-chloroethyl)-1,2,3,4-tetrahydroisoquinoline with diethyl malonate in the presence of tert.—C₄H₉OK in tert.-butanol, saponifying, decarboxylation, and esterification]
1-aminomethyl-6,7-dimethoxy-1,2,3,4-tetrahydroisoquinoline
1-aminomethyl-3-methyl-6,7-dimethoxy-1,2,3,4-tetrahydroisoquinoline
1-aminomethyl-3-ethyl-6,7-dimethoxy-1,2,3,4-tetrahydroisoquinoline, the following final products are obtained by reaction with 3,4,5-trimethoxybenzoyl chloride:

1-(3,4,5-trimethoxybenzamidomethyl)-isoquinoline, m.p. 158°–161° (from isopropanol);
1-(3,4,5-trimethoxybenzamidomethyl)-3-methyl-isoquinoline, m.p. 130°–132° (from isopropanol);
1-(3,4,5-trimethoxybenzamidomethyl)-3-ethyl-isoquinoline;
1-(3,4,5-trimethoxybenzamidomethyl)-3-ethyl-6,7-dimethoxyisoquinoline, m.p. 175°–176°;
1-(3,4,5-trimethoxybenzamidomethyl)-3-ethyl-1,2,3,4-tetrahydroisoquinoline;
1-(3,4,5-trimethoxybenzamidomethyl)-2-benzyl-1,2,3,4-tetrahydroisoquinoline, m.p. 141° (from ethanol);
1-(3,4,5-trimethoxybenzamidomethyl)-2-(2-piperidinoethyl)-1,2,3,4-tetrahydroisoquinoline, m.p. 112°–114° (from ether);
1-(3,4,5-trimethoxybenzamidomethyl)-2-[2-(3,4-dehydropiperidino)-ethyl]-1,2,3,4-tetrahydroisoquinoline, dihydrochloride, m.p. 208°–209°;
1-(3,4,5-trimethoxybenzamidomethyl)-2-(3-carbethoxypropyl)-1,2,3,4-tetrahydroisoquinoline, m.p. 159°–160° (from ethyl acetate);
1-(3,4,5-trimethoxybenzamidomethyl)-6,7-dimethoxy-1,2,3,4-tetrahydroisoquinoline, hydrochloride, m.p. 234°–236°;
1-(3,4,5-trimethoxybenzamidomethyl)-3-methyl-6,7-dimethoxy-1,2,3,4-tetrahydroisoquinoline;
1-(3,4,5-trimethoxybenzamidomethyl)-3-ethyl-6,7-dimethoxy-1,2,3,4-tetrahydroisoquinoline, m.p. 116°–117°.

b. 44.6 g. of 1-(3,4,5-trimethoxybenzamidomethyl)-2-benzyl-1,2,3,4-tetrahydroisoquinoline is hydrogenated in 1.5 l. of methanol at 5 atmospheres on 20 g. of 5% palladium charcoal. The mixture is filtered and evaporated, thus obtaining 1-(3,4,5-trimethoxybenzamidomethyl)-1,2,3,4-tetrahydroisoquinoline, m.p. 127°–130° (from ether).

c. 3.56 g. of 1-(3,4,5-trimethoxybenzamidomethyl)-1,2,3,4-tetrahydroisoquinoline is heated with 1.5 g. of formic acid and 3.5 g. of 35% formaldehyde solution for 45 minutes on a steam bath and then left overnight. The mixture is neutralized with potassium bicarbonate, extracted with chloroform, dried, and evaporated, thus producing 1-(3,4,5-trimethoxybenzamidomethyl)-2-methyl-1,2,3,4-tetrahydroisoquinoline; hydrochloride, m.p. 228°–230°.

Analogously, with formic acid/formaldehyde, the final compounds set forth below are obtained from 1-(3,4,5-trimethoxybenzamidomethyl)-3-methyl-1,2,3,4-tetrahydroisoquinoline or 1-(3,4,5-trimethoxybenzamidomethyl)-3-ethyl-1,2,3,4-tetrahydroisoquinoline, respectively:

1-(3,4,5-trimethoxybenzamidomethyl)-2,3-dimethyl-1,2,3,4-tetrahydroisoquinoline (oil) or
1-(3,4,5-trimethoxybenzamidomethyl)-2-methyl-3-ethyl-1,2,3,4-tetrahydroisoquinoline.

d. A solution of 3.7 g. of 1-(3,4,5-trimethoxybenzamidomethyl)-3-methyl-1,2,3,4-tetrahydroisoquinoline, 9.8 g. of n-butyl bromide, and 10 ml. of triethylamine in 100 ml. of dioxane is refluxed for 3 days. The mixture is then evaporated, taken up in chloroform, and washed with KHCO₃ solution. The chloroform solution is concentrated by evaporation, and the thus-obtained 1-(3,4,5-trimethoxybenzamidomethyl)-2-n-butyl-3-methyl-1,2,3,4-tetrahydroisoquinoline is crystallized with diisopropyl ether; m.p. 81°–83°.

Analogously, the following final products are obtained from the corresponding tetrahydroisoquinolines which are unsubstituted in the 2-position, with the corresponding alkyl bromides or iodides:

1-(3,4,5-trimethoxybenzamidomethyl)-2-n-propyl-1,2,3,4-tetrahydroisoquinoline 1-(3,4,5-trimethoxybenzamidomethyl)-2-n-propyl-3-methyl-1,2,3,4-tetrahydroisoquinoline 1-(3,4,5-trimethoxybenzamidomethyl)-2-isopropyl-1,2,3,4-tetrahydroisoquinoline 1-(3,4,5-trimethoxybenzamidomethyl)-2-isopropyl-3-methyl-1,2,3,4-tetrahydroisoquinoline.

e. A solution of 3.56 g. of 1-(3,4,5-trimethoxybenzamidomethyl)-1,2,3,4-tetrahydroisoquinoline and 1.45 g. of acetic anhydride in 65 ml. of pyridine is allowed to stand overnight; then, the mixture is evaporated and worked up with chloroform and potassium bicarbonate solution, thus obtaining 1-(3,4,5-trimethoxybenzamidomethyl)-2-acetyl-1,2,3,4-tetrahydroisoquinoline, m.p. 196°–197°.

Analogously, by reaction with the corresponding acid anhydrides or chlorides, the following final products are obtained from the corresponding 1,2,3,4-tetrahydroisoquinolines unsubstituted in the 2-position:

1-(3,4,5-trimethoxybenzamidomethyl)-2-acetyl-3-methyl-1,2,3,4-tetrahydroisoquinoline 1-(3,4,5-trimethoxybenzamidomethyl)-2-propionyl-1,2,3,4-tetrahydroisoquinoline 1-(3,4,5-trimethoxybenzamidomethyl)-2-butyryl-1,2,3,4-tetrahydroisoquinoline 1-(3,4,5-trimethoxybenzamidomethyl)-2-heptanoyl-1,2,3,4-tetrahydroisoquinoline 1-(3,4,5-trimethoxybenzamidomethyl)-2-heptanoyl-3-methyl-1,2,3,4-tetrahydroisoquinoline 1-(3,4,5-trimethoxybenzamidomethyl)-2-benzoyl-1,2,3,4-tetrahydroisoquinoline, m.p. 161°–163°

1-(3,4,5-trimethoxybenzamidomethyl)-2-benzoyl-3-methyl-1,2,3,4-tetrahydroisoquinoline 1-(3,4,5-trimethoxybenzamidomethyl)-2-p-methoxybenzoyl-1,2,3,4-tetrahydroisoquinoline, m.p. 160°–162°

1-(3,4,5-trimethoxybenzamidomethyl)-2-p-methoxybenzoyl-3-methyl-1,2,3,4-tetrahydroisoquinoline.

f. 3.52 g. of 1-(3,4,5-trimethoxybenzamidomethyl)isoquinoline is heated to 50° for 2 days with 4.5 ml. of methyl iodide in 120 ml. of acetonitrile. During the concentration of the solution, the thus-produced 1-(3,4,5-trimethoxybenzamidomethyl)-2-methyl-isoquinolinium iodide is crystallized, m.p. 213°–215° (from methanol).

Analogously, the following final compounds are obtained from the corresponding isoquinolines with methyl iodide, ethyl bromide, and n-butyl bromide, respectively:

1-(3,4,5-trimethoxybenzamidomethyl)-2,3-dimethylisoquinolinium iodide 1-(3,4,5-trimethoxybenzamidomethyl)-2-ethylisoquinolinium bromide 1-(3,4,5-trimethoxybenzamidomethyl)-2-ethyl-3-methylisoquinolinium bromide 1-(3,4,5-trimethoxybenzamidomethyl)-2-n-butylisoquinolinium bromide 1-(3,4,5-trimethoxybenzamidomethyl)-2-n-butyl-3-methylisoquinolinium bromide.

g. A solution of 4.94 g. of 1-(3,4,5-trimethoxybenzamidomethyl)-2-methyl-isoquinolinium iodide in 60 ml of methanol is hydrogenated on 1 g. of 5% palladium charcoal at 45° and 2 atmospheres. The reaction product is filtered and evaporated, thus obtaining 1-(3,4,5-trimethoxybenzamidomethyl)-2-methyl-1,2,3,4-tetrahydroisoquinoline; hydrochloride, m.p. 228°–230°.

Analogously, the following final products are obtained by the hydrogenation of the corresponding quaternary salts:

1-(3,4,5-trimethoxybenzamidomethyl)-2,3-dimethyl-1,2,3,4-tetrahydroisoquinoline 1-(3,4,5-trimethoxybenzamidomethyl)-2-ethyl-1,2,3,4-tetrahydroisoquinoline 1-(3,4,5-trimethoxybenzamidomethyl)-2-ethyl-3-methyl-1,2,3,4-tetrahydroisoquinoline 1-(3,4,5-trimethoxybenzamidomethyl)-2-n-butyl-1,2,3,4-tetrahydroisoquinoline 1-(3,4,5-trimethoxybenzamidomethyl)-2-n-butyl-3-methyl-1,2,3,4-tetrahydroisoquinoline, m.p. 81°–83°.

h. One gram of 1-(3,4,5-trimethoxybenzamidomethyl)-3-methyl-isoquinoline is hydrogenated in 30 ml. of methanol on 100 mg. of PtO$_2$ at 60° and under normal pressure. The reaction product is filtered and evaporated, thus producing 1-(3,4,5-trimethoxybenzamidomethyl)-3-methyl-1,2,3,4-tetrahydroisoquinoline, m.p. 162°–164°.

EXAMPLE 2

A solution of 20.6 g. of 1-aminomethyl-2-(2-hydroxyethyl)-1,2,3,4-tetrahydroisoquinoline and 27.6 g. of 3,4,5-trimethoxybenzoyl chloride in 130 ml. of pyridine is left to stand overnight. The thus-precipitated 1-(3,4,5-trimethoxybenzamidomethyl)-2-[2-(3,4,5-trimethoxybenzoyloxy)-ethyl]-1,2,3,4-tetrahydroisoquinoline is filtered, washed with ether, and extracted with methanol; m.p. 236°–238°. The pyridine filtrate is evaporated, the residue is taken up in chloroform and washed several times with 5% potassium bicarbonate solution. After drying and evaporation, 1-(3,4,5-trimethoxybenzamidomethyl)-2-(2-hydroxyethyl)-1,2,3,4-tetrahydroisoquinoline is obtained in this way; m.p. 138°–140° (from ethyl acetate).

EXAMPLE 3

A solution of 21.9 g. of 1-aminomethyl-2-(3-aminopropyl)-1,2,3,4-tetrahydroisoquinoline and 70 g. of 3,4,5-trimethoxybenzoyl chloride is allowed to stand in 300 ml. of pyridine for 2 days. The mixture is then evaporated, the residue taken up in chloroform and repeatedly washed with 5% potassium bicarbonate solution. After drying and evaporation, the thus-obtained 1-(3,4,5-trimethoxybenzamidomethyl)-2-[3-(3,4,5-trimethoxybenzamido)-propyl]-1,2,3,4-tetrahydroisoquinoline is chromatographed on silica gel (eluting agent chloroform/methanol 97:3). The product is amorphous.

EXAMPLE 4

A solution of 30.5 g. of 1-aminomethyl-2-(2-hydroxy-3-morpholinopropyl)-1,2,3,4-tetrahydroisoquinoline [trihydrochloride, m.p. 245°–247°; obtainable by reacting 1-benzamidomethyl-2-(2-hydroxy-3-chloropropyl)-1,2,3,4-tetrahydroisoquinoline with morpholine and hydrolyzing the thus-produced 1-benzamidomethyl-2-(2-hydroxy-3-morpholinopropyl)-1,2,3,4-tetrahydroisoquinoline (hydrochloride, m.p. 203° from ethanol) with hydrochloric acid; an isomeric 1-aminomethyl-2-(2-hydroxy-3-morpholinopropyl)-1,2,3,4-tetrahydroisoquinoline is thus obtained; trihydrochloride, m.p. 107°–110°] and 46 g. of 3,4,5-trimethoxybenzoyl chloride in 420 ml. of pyridine is allowed to stand for 2 days and then worked up analogously to Example 1, thus obtaining 1-(3,4,5- trimethoxybenzamidomethyl)-2-[2-(3,4,5-trimethoxybenzoyloxy)-3-morpholinopropyl]-1,2,3,4-tetrahydroisoquinoline, m.p. 138°–139° (from ethyl acetate).

EXAMPLE 5

Analogously to Example 1(a), the oily (+)-1-(3,4,5-trimethoxybenzamidomethyl)-3-methyl-1,2,3,4-tetrahydroisoquinoline, $[\alpha]_D^{20}$ +15.3° (in methanol) is obtained from (+)-1-aminomethyl-3-methyl-1,2,3,4-tetrahydroisoquinoline (obtainable by splitting the inactive amine with tartaric acid).

From (−)-1-aminomethyl-3-methyl-1,2,3,4-tetrahydroisoquinoline, it is correspondingly possible to produce the oily (−)-1-(3,4,5-trimethoxybenzamidomethyl)-3-methyl-1,2,3,4-tetrahydroisoquinoline; $[\alpha]_D^{20}$ −15.3° (in methanol).

EXAMPLE 6

3.64 g. of 1-cyano-2-(3,4,5-trimethoxybenzoyl)-3-methyl-1,2-dihydroisoquinoline (obtainable by adding aqueous NaCN solution to a solution of 3-methylisoquinoline in methylene chloride and dropwise addition of 3,4,5-trimethoxybenzoyl chloride) is hydrogenated in 150 ml. of ethyl acetate on 5 g. of Raney nickel at 100 atmospheres and 80° for 21 hours. The mixture is then filtered and evaporated, thus producing 1-(3,4,5-trimethoxybenzamidomethyl)-3-methyl-1,2,3,4-tetrahydroisoquinoline, m.p. 162°–164°; hydrochloride, m.p. 192°–194°

EXAMPLE 7

A mixture of 1.81 g. of 2-(3,4-dimethoxyphenyl)-ethylamine, 3.27 g. of 3,4,5-trimethoxybenzamidoacetaldehyde diethylacetal (obtainable from aminoacetaldehyde diethylacetal and 3,4,5-trimethoxybenzoyl chloride) and 20 ml. of 70% formic acid is heated for 8 hours to 100°. The mixture is then evaporated, the residue dissolved in chloroform, washed with $KHCO_3$ solution, and chromatographed on silica gel (eluting agent chloroform/methanol 19:1), thus obtaining 1-(3,4,5-trimethoxybenzamidomethyl)-6,7-dimethoxy-1,2,3,4-tetrahydroisoquinoline; hydrochloride, m.p. 234°–236°.

EXAMPLE 8

4.48 g. of α-(3,4,5-trimethoxybenzamido)-N-[2-hydroxy-2-(3,4-dimethoxyphenyl)-ethyl]-acetamide [producible from 2-(3,4-dimethoxyphenyl)-2-hydroxyethylamine and 3,4,5-trimethoxybenzamidoacetyl chloride] is allowed to stand in 100 ml. of chloroform with 6.2 g. of phosphorus pentachloride for 3 days at 20°. The mixture is decomposed with ice water and washed several times with $NaHCO_3$ solution. The chloroform solution is evaporated. The thus-obtained crude 1-(3,4,5-trimethoxybenzamidomethyl)-6,7-dimethoxyisoquinoline is taken up in 50 ml. of methanol, combined with 400 mg. of $PtO_2$, and hydrogenated at 20° and under normal pressure. The product is filtered and evaporated. Chromatography on silica gel (with chloroform/methanol 19:1) yields 1-(3,4,5-trimethoxybenzamidomethyl)-6,7-dimethoxy-1,2,3,4-tetrahydroisoquinoline; hydrochloride, m.p. 234°–236°.

EXAMPLE 9

A mixture of 2.0 g. of 1-(3,4-dimethoxyphenyl)-2-chloroethane and 2.5 g of 3,4,5-trimethoxybenzamidoacetonitrile (obtainable from aminoacetonitrile and 3,4,5-trimethoxybenzoyl chloride) is allowed to stand overnight at 20° in 100 ml. of o-dichlorobenzene and with 2.6 g. of tin tetrachloride; the mixture is thereafter heated for 3 hours to 110°. The solution is concentrated by evaporation, and the residue is shaken with chloroform and sodium hydroxide solution. The chloroform solution is evaporated, and the thus-obtained crude 1-(3,4,5-trimethoxybenzamidomethyl)-6,7-dimethoxy-3,4-dihydroisoquinoline is dissolved in 30 ml. of methanol and hydrogenated with 200 mg. of $PtO_2$ at 20° and under normal pressure. After filtration, evaporation, and purification by chromatography on silica gel, 1-(3,4,5-trimethoxybenzamidomethyl)-6,7-dimethoxy-1,2,3,4-tetrahydroisoquinoline is obtained; hydrochloride, m.p. 234°–236°.

The following examples relate to pharmaceutical preparations containing compounds of general Formula I:

EXAMPLE A

Tablets

A mixture consisting of 100 kg. of 1-(3,4,5-trimethoxybenzamidomethyl)-3-methyl-1,2,3,4-tetrahydroisoquinoline, 400 kg. of lactose, 145 kg. of wheat starch, 20 kg. of talc, and 15 kg. of magnesium stearate is compressed into tablets as usual, so that each tablet contains 100 mg. of the active ingredient.

EXAMPLE B

Dragees

Analogously to Example A, tablets are compressed and then coated in the usual way with a layer consisting of sugar, corn starch, talc, and tragacanth.

In an analogous manner, tablets and dragees can be obtained which contain one or more of the other effective agents of Formula I and/or the physiologically acceptable acid addition salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An isoquinoline of the formula

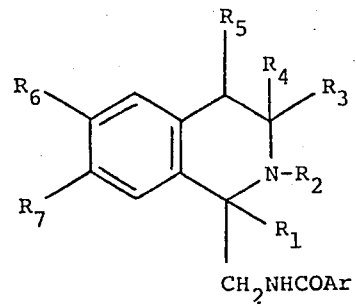

wherein $R_1$ and $R_2$ each are H or $R_1$ is H and $R_2$ is $R_8$ or $R_1$ and $R_2$ collectively are a C—N bond, $R_3$ is H, methyl or ethyl, $R_4$ and $R_5$ each are H or collectively a C—C bond, $R_6$ and $R_7$ each are H or methoxy, and Ar is 3,4,5-trimethoxyphenyl, $R_8$ being the acryl radical of an organic carboxylic acid of 1–10 carbon atoms, alkyl of 1–17 carbon atoms, or the corresponding alkyl substituted by one of phenyl, OH, ArCOO—, ArCONH—, piperidino, 3,4-dehydropiperidino, carboxy, carbomethoxy and carbethoxy, Ar in each instance being 3,4,5-trimethoxyphenyl, the physiologically acceptable acid addition salts thereof.

2. A free base of claim 1 wherein $R_1$, $R_2$, $R_3$, $R_4$ and $R_5$ each are H, or a physiologically acceptable acid addition salt thereof.

3. A free base of claim 1 wherein $R_6$ and $R_7$ each are, or a physiologically acceptable acid addition salt thereof.

4. A free base of claim 1 wherein $R_3$ is H or $CH_3$, or a physiologically acceptable acid addition salt thereof.

5. A free base of claim 2 wherein $R_6$ and $R_7$ each are H and $R_3$ is H or $CH_3$, or a physiologically acceptable acid addition salt thereof.

6. A free base of claim 1 wherein $R_6$ and $R_7$ each are methoxy, or a physiologically acceptable acid addition salt thereof.

7. A compound of claim 1, 1-(3,4,5-trimethoxybenzamidomethyl)-3-methyl-1,2,3,4-tetrahydroisoquinoline or a physiologically acceptable acid addition salt thereof.

8. A compound of claim 1, 1-(3,4,5-trimethoxybenzamidomethyl)-isoquinoline.

9. A compound of claim 1, 1-(3,4,5-trimethoxybenzamidomethyl)-3-methyl-isoquinoline.

10. A compound of claim 1, 1-(3,4,5-trimethoxybenzamidomethyl)-3-ethyl-6,7-dimethoxy-isoquinoline.

11. A compound of claim 1, 1-(3,4,5-trimethoxybenzamidomethyl)-2-benzyl-1,2,3,4-tetrahydroisoquinoline.

12. A compound of claim 1, 1-(3,4,5-trimethoxybenzamidomethyl)-2-(2-piperidinoethyl)-1,2,3,4-tetrahydroisoquinoline.

13. A compound of claim 1, 1-(3,4,5-trimethoxybenzamidomethyl)-2-[2-(3,4-dehydropiperidino)-ethyl]-1,2,3,4-tetrahydroisoquinoline dihydrochloride.

14. A compound of claim 1, 1-(3,4,5-trimethoxybenzamidomethyl)-2-(3-carbethoxypropyl)-1,2,3,4-tetrahydroisoquinoline.

15. A compound of claim 1, 1-(3,4,5-trimethoxybenzamidomethyl)-6,7-dimethoxy-1,2,3,4-tetrahydroisoquinoline hydrochloride.

16. A compound of claim 1, 1-(3,4,5-trimethoxybenzamidomethyl)-3-ethyl-6,7-dimethoxy-1,2,3,4-tetrahydroisoquinoline.

17. A compound of claim 1, 1-(3,4,5-trimethoxybenzamidomethyl)-1,2,3,4-tetrahydroisoquinoline.

18. A compound of claim 1, 1-(3,4,5-trimethoxybenzamidomethyl)-2-methyl-1,2,3,4-tetrahydroisoquinoline.

19. A compound of claim 1, 1-(3,4,5-trimethoxybenzamidomethyl)-2-n-butyl-3-methyl-1,2,3,4,-tetrahydroisoquinoline.

20. A compound of claim 1, 1-(3,4,5-trimethoxybenzamidomethyl)-2-acetyl-1,2,3,4-tetrahydroisoquinoline.

21. A compound of claim 1, 1-(3,4,5-trimethoxybenzamidomethyl)-2-benzoyl-1,2,3,4-tetrahydroisoquinoline.

22. A compound of claim 1, 1-(3,4,5-trimethoxybenzamidomethyl)-2-p-methoxybenzoyl-1,2,3,4-tetrahydroisoquinoline.

23. A compound of claim 1, 1-(3,4,5-trimethoxybenzamidomethyl)-2-methyl-1,2,3,4-tetrahydroisoquinoline hydrochloride.

24. A compound of claim 1, 1-(3,4,5-trimethoxybenzamidomethyl)-2-[2-(3,4,5-trimethoxybenzoyloxy)-ethyl]-1,2,3,4-tetrahydroisoquinoline.

25. A compound of claim 1, 1-(3,4,5-trimethoxybenzamidomethyl)-2-(2-hydroxyethyl)-1,2,3,4-tetrahydroisoquinoline.

26. A compound of claim 1, 1-(3,4,5-trimethoxybenzamidomethyl)-2-[3-(3,4,5-trimethoxybenzamido)-propyl]-1,2,3,4-tetrahydroisoquinoline.

27. A pharmaceutical composition for the treatment of cardiovascular diseases comprising an amount from 20 to 500 mg. per unit dosage of a compound of claim 1 in admixture with a pharmaceutically acceptable carrier adapted for oral administration.

* * * * *